United States Patent
Uchida et al.

(10) Patent No.: US 10,723,107 B2
(45) Date of Patent: Jul. 28, 2020

(54) ELASTIC LAMINATE AND ARTICLE CONTAINING SAME

(71) Applicant: NITTO DENKO CORPORATION, Ibaraki-shi, Osaka (JP)

(72) Inventors: Shou Uchida, Ibaraki (JP); Shinsuke Ikishima, Ibaraki (JP); Kohei Takeda, Ibaraki (JP); Masaaki Arakawa, Ibaraki (JP)

(73) Assignee: NITTO DENKO CORPORATION, Ibaraki-shi, Osaka (JP)

( * ) Notice: Subject to any disclaimer, the term of this patent is extended or adjusted under 35 U.S.C. 154(b) by 130 days.

(21) Appl. No.: 15/110,980

(22) PCT Filed: Aug. 18, 2015

(86) PCT No.: PCT/JP2015/073103
§ 371 (c)(1),
(2) Date: Jul. 12, 2016

(87) PCT Pub. No.: WO2016/031621
PCT Pub. Date: Mar. 3, 2016

(65) Prior Publication Data
US 2017/0157901 A1 Jun. 8, 2017

(30) Foreign Application Priority Data

Aug. 26, 2014 (JP) ................... 2014-171496
Jul. 17, 2015 (JP) ................... 2015-143007

(51) Int. Cl.
| | | |
|---|---|---|
| B32B 27/12 | (2006.01) | |
| A41D 13/11 | (2006.01) | |
| B32B 7/02 | (2019.01) | |
| A41D 13/00 | (2006.01) | |
| B32B 25/10 | (2006.01) | |
| A61F 13/56 | (2006.01) | |

(Continued)

(52) U.S. Cl.
CPC .............. B32B 27/12 (2013.01); A41D 13/00 (2013.01); A41D 13/11 (2013.01);
(Continued)

(58) Field of Classification Search
CPC .................................. B32B 27/12; A61F 3/514
(Continued)

(56) References Cited

U.S. PATENT DOCUMENTS 6,255,236 B1 7/2001 Cree et al.
6,329,468 B1 12/2001 Wang
(Continued)

FOREIGN PATENT DOCUMENTS

CN 1400940 A 3/2003
CN 102498170 A 6/2012
(Continued)

OTHER PUBLICATIONS

The State Intellectual Property Office of P.R. China issued in CN Application No. 201580010694.X dated Apr. 2, 2018.
(Continued)

*Primary Examiner* — Peter Y Choi
(74) *Attorney, Agent, or Firm* — Sughrue Mion, PLLC (57) ABSTRACT

Provided is a stretchable laminate which has a sufficient holding ability in the case of being stretched to be bonded onto another material and is excellent in feeling of touch. Also provided is an article including such stretchable laminate. The stretchable laminate of the present invention is a stretchable laminate, including: an elastomer layer; and a non-woven fabric layer arranged on at least one side of the elastomer layer, the stretchable laminate including an elastic lane portion and a rigid lane portion, the rigid lane portion requiring a strength of from 1 N/20 mm to 7 N/20 mm for obtaining a 5% deformation amount.

19 Claims, 3 Drawing Sheets

(51) Int. Cl.
*A61F 13/49* (2006.01)
*A61F 13/15* (2006.01)
*A61F 13/514* (2006.01)
*B32B 5/02* (2006.01)
*B32B 7/12* (2006.01)
*B32B 27/30* (2006.01)
*D04H 1/492* (2012.01)

(52) U.S. Cl.
CPC .... *A61F 13/15699* (2013.01); *A61F 13/4902* (2013.01); *A61F 13/49015* (2013.01); *A61F 13/51478* (2013.01); *A61F 13/5633* (2013.01); *B32B 5/022* (2013.01); *B32B 7/02* (2013.01); *B32B 7/12* (2013.01); *B32B 25/10* (2013.01); *B32B 27/302* (2013.01); *D04H 1/492* (2013.01); *A61F 2013/49022* (2013.01); *B32B 2250/02* (2013.01); *B32B 2255/10* (2013.01); *B32B 2255/26* (2013.01); *B32B 2274/00* (2013.01); *B32B 2307/51* (2013.01); *B32B 2307/54* (2013.01); *B32B 2437/00* (2013.01); *B32B 2555/02* (2013.01); *D10B 2501/042* (2013.01); *D10B 2509/026* (2013.01)

(58) Field of Classification Search
USPC .................................................. 442/149, 151
See application file for complete search history.

(56) References Cited

U.S. PATENT DOCUMENTS

| | | | | |
|---|---|---|---|---|
| 7,348,376 | B2 * | 3/2008 | Gelles | .................. A61L 15/585 |
| | | | | 524/505 |
| 7,794,819 | B2 * | 9/2010 | Black | .................... B32B 37/144 |
| | | | | 428/189 |
| 8,921,474 | B2 | 12/2014 | Alper et al. | |
| 9,138,959 | B2 | 9/2015 | Marche et al. | |
| 2003/0194936 | A1 * | 10/2003 | Jackson | .................. A61F 13/58 |
| | | | | 442/327 |
| 2006/0259003 | A1 * | 11/2006 | Venkitaraman | ... A61F 13/49015 |
| | | | | 604/385.22 |
| 2011/0021103 | A1 | 1/2011 | Alper et al. | |
| 2013/0177741 | A1 | 7/2013 | Marche et al. | |
| 2014/0045401 | A1 | 2/2014 | Kunihiro et al. | |
| 2014/0343522 | A1 | 11/2014 | Arai et al. | |

FOREIGN PATENT DOCUMENTS

| | | |
|---|---|---|
| CN | 103209829 A | 7/2013 |
| EP | 2 158 888 A1 | 3/2010 |
| JP | 09-075394 A | 3/1997 |
| JP | 2001-079970 A | 3/2001 |
| JP | 2003-533551 A | 11/2003 |
| JP | 3830818 B2 | 10/2006 |
| JP | 2012-187857 A | 10/2012 |
| JP | 2013-500359 A | 1/2013 |
| JP | 2013-126431 A | 6/2013 |
| WO | 01/53076 A1 | 7/2001 |

OTHER PUBLICATIONS

International Search Report of PCT/JP2015/073103 dated Nov. 24, 2015.

Extended European Search Report dated Jun. 29, 2017 from the European Patent Office in counterpart application No. 15834829.2.

* cited by examiner

ELASTIC LAMINATE AND ARTICLE CONTAINING SAME

TECHNICAL FIELD

The present invention relates to a stretchable laminate and an article including the stretchable laminate.

BACKGROUND ART

Various stretchable laminates are proposed for materials for articles such as sanitary articles, for example, diapers and masks (see, for example, Patent Literatures 1 and 2).

As such materials, a stretchable laminate including an elastomer layer and a non-woven fabric layer arranged on at least one side of the elastomer layer has been proposed. In such stretchable laminate, the elastomer layer and the non-woven fabric layer are generally bonded onto each other with an adhesive or a pressure-sensitive adhesive.

However, the related-art stretchable laminate including an elastomer layer and a non-woven fabric layer arranged on at least one side of the elastomer layer has a problem in that the stretchable laminate does not have a sufficient holding ability in the case of being stretched to be bonded onto another material, and hence is significantly deformed or peeled. For example, in the case where the stretchable laminate is used as an ear portion of a disposable diaper, when the ear portion is significantly deformed or peeled, there arises a problem such as slipping-down.

Further, it is important for such stretchable laminate to have an excellent feeling of touch so as to be comfortably fitted to each of various users.

CITATION LIST

Patent Literature

[PTL 1] JP 2012-187857 A
[PTL 2] JP 3830818 B2

SUMMARY OF INVENTION

Technical Problem

The present invention has been made to solve the problems of the related art, and an object of the present invention is to provide a stretchable laminate which has a sufficient holding ability in the case of being stretched to be bonded onto another material and is excellent in feeling of touch. Another object of the present invention is to provide an article including such stretchable laminate.

Solution to Problem

A stretchable laminate according to one embodiment of the present invention is a stretchable laminate, including: an elastomer layer; and a non-woven fabric layer arranged on at least one side of the elastomer layer, the stretchable laminate including an elastic lane portion and a rigid lane portion, the rigid lane portion requiring a strength of from 1 N/20 mm to 7 N/20 mm for obtaining a 5% deformation amount.

In a preferred embodiment, the rigid lane portion requires a strength of from 1 N/20 mm to 4 N/20 mm for obtaining a 5% deformation amount.

In a preferred embodiment, the rigid lane portion includes an end portion of the stretchable laminate.

In a preferred embodiment, the rigid lane portion has a length from the end portion of the stretchable laminate of from 5 mm to 30 mm.

In a preferred embodiment, the stretchable laminate further includes a hot-melt pressure-sensitive adhesive between the elastomer layer and the non-woven fabric layer.

In a preferred embodiment, the hot-melt pressure-sensitive adhesive in the rigid lane portion contains an olefin-based polymer.

In a preferred embodiment, the olefin-based polymer includes a propylene/1-butene copolymer.

In a preferred embodiment, the hot-melt pressure-sensitive adhesive in the rigid lane portion contains the olefin-based polymer and the same kind of polymer as an elastomer resin forming the elastomer layer.

In a preferred embodiment, the polymer of the same kind as the elastomer resin forming the elastomer layer includes a styrene-based polymer.

In a preferred embodiment, the hot-melt pressure-sensitive adhesive in the elastic lane portion contains a styrene-based polymer.

In a preferred embodiment, the styrene-based polymer contains SIS.

In a preferred embodiment, the hot-melt pressure-sensitive adhesive in the elastic lane portion has a stripe shape.

In a preferred embodiment, the elastomer layer includes a styrene-based elastomer.

In a preferred embodiment, the styrene-based elastomer includes an SIS-based elastomer.

In a preferred embodiment, the SIS-based elastomer has a content of styrene of from 3 wt % to 60 wt %.

In a preferred embodiment, the SIS-based elastomer has a content of styrene of from 10 wt % to 50 wt %.

In a preferred embodiment, the SIS-based elastomer has a MFR of from 5.0 g/10 min to 25.0 g/10 min.

In a preferred embodiment, the SIS-based elastomer has a MFR of from 8.0 g/10 min to 18.0 g/10 min.

In a preferred embodiment, the non-woven fabric layer includes a spunlace non-woven fabric.

An article according to one embodiment of the present invention includes the stretchable laminate according to the one embodiment of the present invention.

DESCRIPTION OF EMBODIMENTS

<<<<Stretchable Laminate>>>>

A stretchable laminate of the present invention is a stretchable laminate including a non-woven fabric layer on at least one side of an elastomer layer. The stretchable laminate of the present invention may include any appropriate other layer to the extent that the effects of the present invention are not impaired as long as the stretchable laminate includes a non-woven fabric layer on at least one side of the elastomer layer. The number of such any appropriate other layers may be only one, or may be two or more.

The stretchable laminate of the present invention may include a material for bonding the elastomer layer and the non-woven fabric layer onto each other between the elastomer layer and the non-woven fabric layer. As such material, there are given, for example, an adhesive, a pressure-sensitive adhesive, and a hot-melt pressure-sensitive adhesive. One kind of those materials may be used alone, or two or more kinds thereof may be used in combination.

The stretchable laminate of the present invention preferably includes a hot-melt pressure-sensitive adhesive between the elastomer layer and the non-woven fabric layer from the viewpoint of enabling the effects of the present invention to be further exhibited. The number of kinds of such hot-melt pressure-sensitive adhesives may be only one, or may be two or more.

The stretchable laminate of the present invention includes an elastic lane portion and a rigid lane portion. When the stretchable laminate of the present invention includes the elastic lane portion and the rigid lane portion that satisfies particular values for physical properties described later, the stretchable laminate can have a sufficient holding ability in the case of being stretched to be bonded onto another material and can be excellent in feeling of touch.

The elastic lane portion is a lane portion having elasticity. The strength required for obtaining a 5% deformation amount of the elastic lane portion is preferably less than 2 N/20 mm, more preferably from 0.1 N/20 mm to 1.5 N/20 mm, still more preferably from 0.1 N/20 mm to 1.0 N/20 mm, particularly preferably from 0.2 N/20 mm to 1.0 N/20 mm, most preferably from 0.2 N/20 mm to 0.8 N/20 mm. When the strength required for obtaining a 5% deformation amount of the elastic lane portion falls within the above-mentioned range, the stretchable laminate can have a further sufficient holding ability in the case of being stretched to be bonded onto another material and can be excellent in fitting feeling.

The rigid lane portion is a lane portion having rigidity. The strength required for obtaining a 5% deformation amount of the rigid lane portion is preferably from 1 N/20 mm to 7N/20 mm, more preferably from 1 N/20 mm to 5 N/20 mm, still more preferably from 1.5 N/20 mm to 4 N/20 mm, particularly preferably from 1.5 N/20 mm to 3 N/20 mm, most preferably from 1.5 N/20 mm to 2.5 N/20 mm. When the strength required for obtaining a 5% deformation amount of the rigid lane portion falls within the above-mentioned range, the stretchable laminate can have a sufficient holding ability in the case of being stretched to be bonded onto another material and can be excellent in feeling of touch. In the present invention, the strength required for obtaining a 5% deformation amount of the rigid lane portion (sometimes referred to as "end portion strength") is measured based on a method described later.

Figure 1:
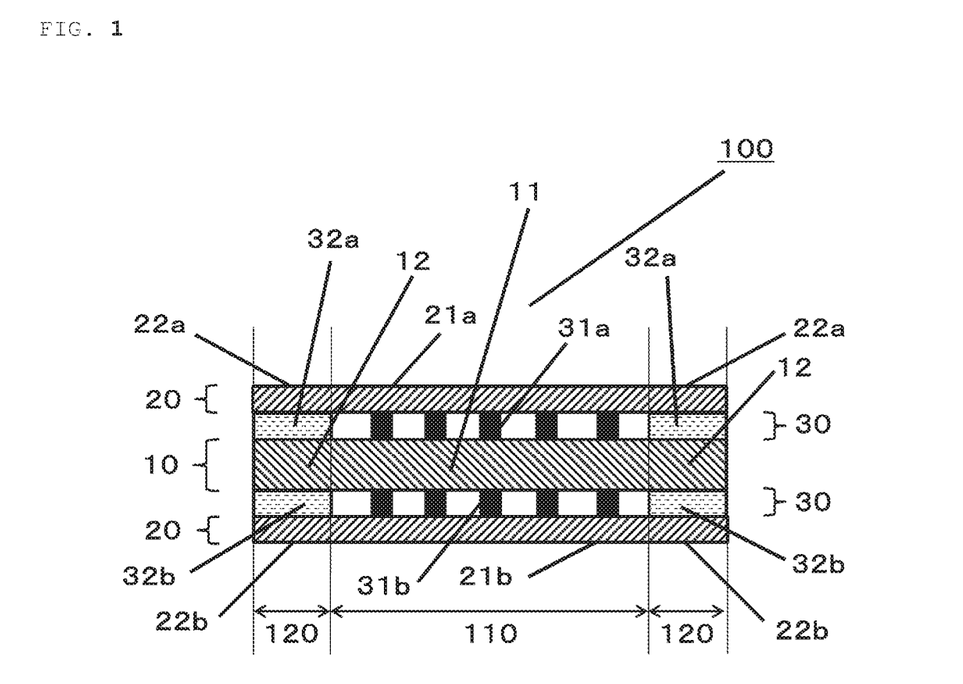
FIG. 1 is a schematic cross-sectional view of a stretchable laminate according to a preferred embodiment of the present invention.

FIG. 1 is a schematic sectional view of a stretchable laminate according to a preferred embodiment of the present invention. A stretchable laminate 100 illustrated in FIG. 1 includes an elastic lane portion 110 and a rigid lane portion 120. The rigid lane portion 120 includes end portions of the stretchable laminate 100. In FIG. 1, the rigid lane portion 120 includes both end portions of the stretchable laminate 100. Unlike FIG. 1, the rigid lane portion 120 may include one end portion of the stretchable laminate 100.

In the embodiment illustrated in FIG. 1, the stretchable laminate 100 includes hot-melt pressure-sensitive adhesives 30 between an elastomer layer 10 and non-woven fabric layers 20. The elastomer layer 10 includes an elastomer layer 11 in the elastic lane portion 110 and an elastomer layer 12 in the rigid lane portion 120. The non-woven fabric layers 20 include non-woven fabric layers 21a and 21b in the elastic lane portion 110 and non-woven fabric layers 22a and 22b in the rigid lane portion 120. The hot-melt pressure-sensitive adhesives 30 include hot-melt pressure-sensitive adhesives 31a and 31b in the elastic lane portion 110 and hot-melt pressure-sensitive adhesives 32a and 32b in the rigid lane portion 120.

The elastic lane portion 110 includes the elastomer layer 11, the non-woven fabric layer 21a arranged on one side of the elastomer layer 11, and the non-woven fabric layer 21b arranged on a side of the elastomer layer 11 opposite to the non-woven fabric layer 21a, and further includes the hot-melt pressure-sensitive adhesive 31a between the elastomer layer 11 and the non-woven fabric layer 21a, and the hot-melt pressure-sensitive adhesive 31b between the elastomer layer 11 and the non-woven fabric layer 21b. In FIG. 1, the hot-melt pressure-sensitive adhesive 31a is illustrated so as to be present in part of a region between the elastomer layer 11 and the non-woven fabric layer 21a, but the hot-melt pressure-sensitive adhesive 31a may be present in the whole region between the elastomer layer 11 and the non-woven fabric layer 21a. Further, similarly, in FIG. 1, the hot-melt pressure-sensitive adhesive 31b is illustrated so as to be present in part of a region between the elastomer layer 11 and the non-woven fabric layer 21b, but the hot-melt pressure-sensitive adhesive 31b may be present in the whole region between the elastomer layer 11 and the non-woven fabric layer 21b.

The rigid lane portion 120 includes the elastomer layer 12, the non-woven fabric layer 22a arranged on one side of the elastomer layer 12, and the non-woven fabric layer 22b arranged on a side of the elastomer layer 12 opposite to the non-woven fabric layer 22a, and further includes the hot-melt pressure-sensitive adhesive 32a between the elastomer layer 12 and the non-woven fabric layer 22a, and the hot-melt pressure-sensitive adhesive 32b between the elastomer layer 12 and the non-woven fabric layer 22b. In FIG. 1, the hot-melt pressure-sensitive adhesive 32a is illustrated so as to be present in the whole region between the elastomer layer 12 and the non-woven fabric layer 22a, but the hot-melt pressure-sensitive adhesive 32a may be present in part of a region between the elastomer layer 12 and the non-woven fabric layer 22a. Further, similarly, in FIG. 1, the hot-melt pressure-sensitive adhesive 32b is illustrated so as to be present in the whole region between the elastomer layer 12 and the non-woven fabric layer 22b, but the hot-melt pressure-sensitive adhesive 32b may be present in part of a region between the elastomer layer 12 and the non-woven fabric layer 22b.

In the stretchable laminate of the present invention, the length of the rigid lane portion from the end portion of the stretchable laminate is preferably from 5 mm to 30 mm, more preferably from 5 mm to 25 mm, still more preferably from 5 mm to 20 mm, particularly preferably from 5 mm to 15 mm, most preferably from 5 mm to 10 mm. In the stretchable laminate of the present invention, when the length of the rigid lane portion falls within the range described above, the stretchable laminate can have a further sufficient holding ability in the case of being stretched to be bonded onto another material and can be more excellent in feeling of touch.

In the stretchable laminate of the present invention, the length of the elastic lane portion may be any appropriate length depending on the purpose. From the viewpoint of enabling the effects of the present invention to be further exhibited, the length of the elastic lane portion is preferably from 5 mm to 150 mm, more preferably from 5 mm to 100 mm, still more preferably from 5 mm to 80 mm, particularly preferably from 10 mm to 60 mm, most preferably from 15 mm to 50 mm.

The thickness of the stretchable laminate of the present invention varies depending on the thickness of the elastomer layer or the thickness of the non-woven fabric layer and is preferably from 2.0 mm to 0.1 mm, more preferably from 1.5 mm to 0.15 mm, still more preferably from 1.0 mm to 0.15 mm, particularly preferably from 0.8 mm to 0.2 mm, most preferably from 0.6 mm to 0.2 mm. When the thickness of the stretchable laminate of the present invention falls within such range, the laminate can be easily used as a material used in articles such as sanitary articles, for example, diapers and masks.

<<Elastomer Layer>>

As the elastomer layer, any appropriate elastomer layer may be adopted to the extent that the effects of the present invention are not impaired. As an elastomer resin serving as a main component in such elastomer layer, there are given, for example, an olefin-based elastomer, a styrene-based elastomer, a vinyl chloride-based elastomer, a urethane-based elastomer, an ester-based elastomer, and an amide-based elastomer.

The elastomer layer includes the elastomer layer in the elastic lane portion and the elastomer layer in the rigid lane portion. The elastomer layer in the elastic lane portion and the elastomer layer in the rigid lane portion may be of the same kind or different kinds. The elastomer layer in the elastic lane portion and the elastomer layer in the rigid lane portion are preferably of the same kind from the viewpoint of enabling the effects of the present invention to be further exhibited. In the following description, the term "elastomer layer" may be read as "elastomer layer in the elastic lane portion" or "elastomer layer in the rigid lane portion".

The content of the elastomer resin serving as a main component in the elastomer layer is preferably from 50 wt % to 100 wt %, more preferably from 70 wt % to 100 wt %, still more preferably from 90 wt % to 100 wt %, particularly preferably from 95 wt % to 100 wt %, most preferably from 98 wt % to 100 wt %. When the content of the elastomer resin serving as a main component in the elastomer layer falls within the range described above, the elastomer layer can exhibit a sufficient elastomer characteristic.

The number of the elastomer layers may be one, or may be two or more. When the elastomer layer has a three-layer structure, for example, it is preferred that the three-layer structure include an intermediate layer in which two or more kinds of elastomers are blended and two surface layers in which the same kinds of elastomers as the elastomers included in the intermediate layer are used.

The elastomer resin serving as a main component in the elastomer layer is preferably a styrene-based elastomer from the viewpoint of enabling the effects of the present invention to be further exhibited.

As the styrene-based elastomer, any appropriate styrene-based elastomer, such as an SIS-based elastomer or an SBS-based elastomer, may be adopted. Such styrene-based elastomer is preferably an SIS-based elastomer having a particular molecular structure from the viewpoint of enabling the effects of the present invention to be further exhibited. Specifically, the SIS-based elastomer is an SIS-based elastomer including a styrene-isoprene-styrene block copolymer molecular structure having different terminal styrene block chain lengths (hereinafter sometimes referred to as "particular SIS-based elastomer") and is discriminated from a conventional SIS-based elastomer. In the present invention, when the particular SIS-based elastomer described above is adopted as as the elastomer resin serving as a main component in the elastomer layer, a stretchable laminate which has a further sufficient holding ability in the case of being stretched to be bonded onto another material and is more excellent in feeling of touch can be provided.

Examples of the particular SIS-based elastomer include products with the trade names "Quintac 3390 (SL-159)" (styrene content=48 wt %) and "Quintac 3620" (styrene content=14 wt %) manufactured by Zeon Corporation.

In the present invention, the content of styrene in the particular SIS-based elastomer serving as a main component in the elastomer layer is more than 3 wt %, preferably from 3 wt % to 60 wt %, more preferably from 3 wt % to 55 wt %, still more preferably from 5 wt % to 55 wt %, particularly preferably from 10 wt % to 50 wt %. When the content of styrene in the particular SIS-based elastomer serving as a main component in the elastomer layer falls within the range described above, a stretchable laminate which has a further sufficient holding ability in the case of being stretched to be bonded onto another material and is more excellent in feeling of touch can be provided.

In the present invention, when the particular SIS-based elastomer is adopted as the elastomer resin, the steps in production of the elastomer layer can be simplified, and hence processing cost can be reduced. This is, for example, because when the other elastomer resin (for example, another styrene-based elastomer) is adopted as the elastomer resin, several kinds of styrene-based elastomers need to be blended with one another in order to control values for physical properties, which needs to prepare a master batch. When the particular SIS-based elastomer is adopted as the elastomer resin, extrusion molding can be performed by using fewer kinds of resins in production of the elastomer layer, which can obviate the need to prepare a master batch.

In the present invention, when the particular SIS-based elastomer is adopted as the elastomer resin, one kind of the particular SIS-based elastomers may be used alone, or two or more kinds thereof may be used as a blend.

In the present invention, the particular SIS-based elastomer which may be adopted as the elastomer resin has a MFR of preferably from 5.0 g/10 min to 25.0 g/10 min, more preferably from 5.0 g/10 min to 23.0 g/10 min, still more preferably from 5.0 g/10 min to 21.0 g/10 min, particularly preferably from 6.0 g/10 min to 20.0 g/10 min, most preferably from 8.0 g/10 min to 18.0 g/10 min. When the particular SIS-based elastomer whose MFR falls within the range described above is adopted, a stretchable laminate which has a further sufficient holding ability in the case of being stretched to be bonded onto another material and is more excellent in feeling of touch can be provided, and the steps in production of the elastomer layer can be simplified, and hence processing cost can be further reduced.

In the present invention, when the elastomer layer has a multilayer structure including two or more layers, the particular SIS-based elastomer may be used in all the layers. Alternatively, the particular SIS-based elastomer may also be used only in a part of the layers, and a styrene-based elastomer except the particular SIS-based elastomer or an olefin-based elastomer may also be used in the other layers.

The elastomer layer may contain any appropriate other component to the extent that the effects of the present invention are not impaired. Examples of such other component include any other polymer, a tackifier, a plasticizer, an antidegradant, a pigment, a dye, an antioxidant, an antistatic agent, a lubricant, a blowing agent, a heat stabilizer, a light stabilizer, an inorganic filler, and an organic filler. The number of kinds of those components may be only one, or may be two or more. The content of the other component in the elastomer layer is preferably 10 wt % or less, more preferably 7 wt % or less, still more preferably 5 wt % or less, particularly preferably 2 wt % or less, more particularly preferably 1 wt % or less.

The thickness of the elastomer layer is preferably from 20 µm to 200 µm, more preferably from 30 µm to 160 µm, still more preferably from 30 µm to 140 µm, yet still more preferably from 30 µm to 120 µm, even yet still more preferably from 30 µm to 100 µm, particularly preferably from 30 µm to 80 µm, most preferably from 30 µm to 60 µm. When the thickness of the elastomer layer falls within such range, a stretchable laminate which has a further sufficient holding ability in the case of being stretched to be bonded onto another material and is more excellent in feeling of touch can be provided.

<<Non-Woven Fabric Layer>>

Any appropriate non-woven fabric layer may be adopted as the non-woven fabric layer to the extent that the effects of the present invention are not impaired. The number of kinds of non-woven fabrics forming the non-woven fabric layer may be only one, or may be two or more.

Examples of the non-woven fabric forming the non-woven fabric layer include a spunbond non-woven web, a raised non-woven fabric (such as a non-woven fabric obtained by a thermal bonding method, a bonding joining method, a spunlace method, or an air-through method), a melt-blown non-woven web, a spunlace non-woven web, a spunbond melt-blown spunbond non-woven web, a spunbond melt-blown melt-blown spunbond non-woven web, an unjoined non-woven web, an electrospun non-woven web, a flashspun non-woven web (such as TYVEK™ of DuPont), and a carded non-woven fabric. Of those non-woven fabrics, a non-woven fabric obtained by a spunlace method, that is, a spunlace non-woven fabric is preferred from the viewpoint of enabling the effects of the present invention to be further exhibited.

The non-woven fabric forming the non-woven fabric layer may contain polyolefin fibers, such as polypropylene, polyethylene, polyester, polyamide, polyurethane, an elastomer, rayon, cellulose, acryl, copolymers thereof, blends thereof, or mixtures thereof.

The non-woven fabric forming the non-woven fabric layer may contain a fiber which has a uniform structure and may contain a two-component structure, such as a sheath/core structure, a side-by-side structure, a sea-island structure, or any other two-component structure. Detailed descriptions of the non-woven fabric can be found in, for example, "Nonwoven Fabric Primer and Reference Sampler," E. A. Vaughn, Association of the Nonwoven Fabrics Industry, third edition (1992).

The basis amount of the non-woven fabric forming the non-woven fabric layer is preferably 150 gsm or less, more preferably 100 gsm or less, still more preferably 50 gsm or less, particularly preferably from 10 gsm to 50 gsm, most preferably from 20 gsm to 40 gsm.

<<Hot-Melt Pressure-Sensitive Adhesive>>

The stretchable laminate of the present invention preferably includes the hot-melt pressure-sensitive adhesive between the elastomer layer and the non-woven fabric layer. When the hot-melt pressure-sensitive adhesive is used, the need to add a tackifier as a component of the elastomer layer is obviated, and hence, for example, the extrusion stability is enhanced, a problem of adhesion of the tackifier to a forming roll can be suppressed, and a problem of contamination of the production line by volatile matter contamination or the like caused by the tackifier can be suppressed.

When the hot-melt pressure-sensitive adhesive is used for bonding the elastomer layer and the non-woven fabric layer, the hot-melt pressure-sensitive adhesive may be present over the whole surface of the non-woven fabric layer or may be present in part of the surface of the non-woven fabric layer. When the hot-melt pressure-sensitive adhesive is present in part of the surface of the non-woven fabric layer, the hot-melt pressure-sensitive adhesive is preferably present so as to include at least an end portion of the non-woven fabric layer.

The stretchable laminate of the present invention includes the elastic lane portion and the rigid lane portion. The hot-melt pressure-sensitive adhesive which may be included in the elastic lane portion (for example, the hot-melt pressure-sensitive adhesives 31a and 31b in FIG. 1) and the hot-melt pressure-sensitive adhesive which may be included in the rigid lane portion (for example, the hot-melt pressure-sensitive adhesives 32a and 32b in FIG. 1) are preferably different kinds of hot-melt pressure-sensitive adhesives. When the hot-melt pressure-sensitive adhesive which may be included in the elastic lane portion and the hot-melt pressure-sensitive adhesive which may be included in the rigid lane portion are different kinds of hot-melt pressure-sensitive adhesives, a stretchable laminate which has a further sufficient holding ability in the case of being stretched to be bonded onto another material and is more excellent in feeling of touch can be provided.

Figure 2:
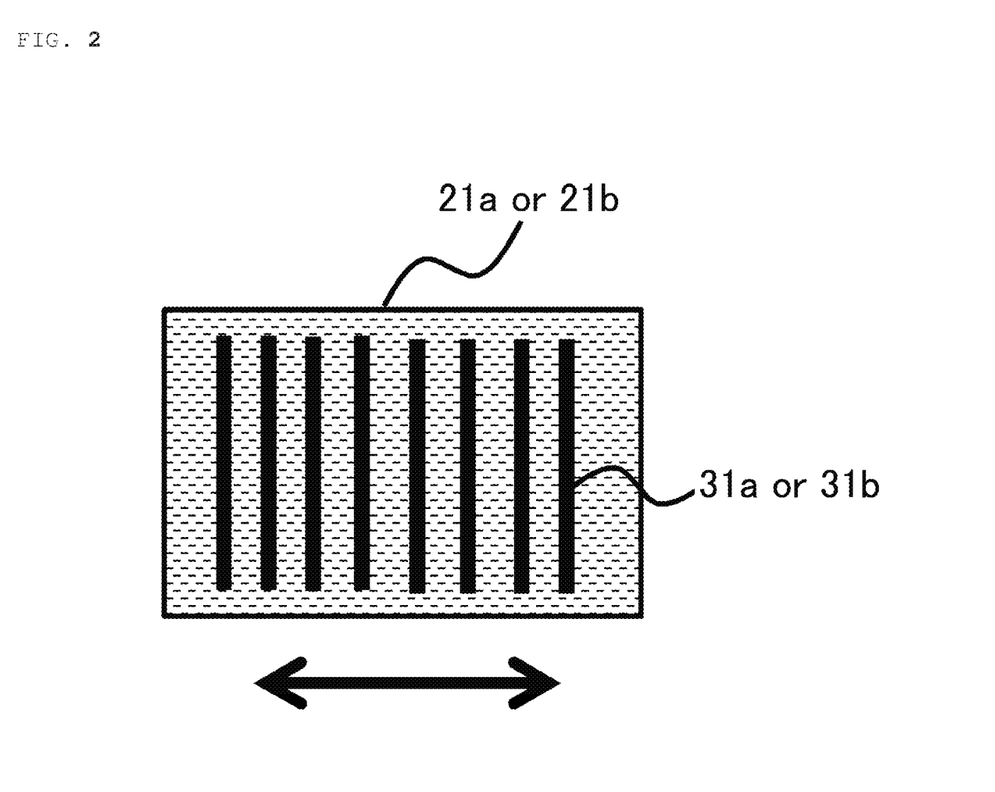
FIG. 2 is a schematic view of a state in which a non-woven fabric is coated with a hot-melt pressure-sensitive adhesive in a striped manner in a flow direction of a production line as viewed from a top surface thereof.

In the hot-melt pressure-sensitive adhesive which may be included in the elastic lane portion, for example, as illustrated in FIG. 2, the hot-melt pressure-sensitive adhesive 31a or 31b may be present in a striped manner or in a dotted manner on the non-woven fabric layer 21a or 21b in a flow direction of the production line. When the hot-melt pressure-sensitive adhesive is present in a striped manner, portions in which the hot-melt pressure-sensitive adhesive is present and portions in which the hot-melt pressure-sensitive adhesive is absent are formed in a striped manner, and therefore, particularly in a direction perpendicular to the stripe pattern (in the direction of the arrow in FIG. 2), the stretchability of the stretchable laminate can be further enhanced.

The hot-melt pressure-sensitive adhesive which may be included in the rigid lane portion may be formed in such a striped manner as in FIG. 2 or may be formed over the whole surface of the non-woven fabric layer (22a or 22b in FIG. 1). The hot-melt pressure-sensitive adhesive which may be included in the rigid lane portion is preferably formed over the whole surface of the non-woven fabric layer (22a or 22b in FIG. 1) from the viewpoint of enabling the effects of the present invention to be further exhibited.

As the hot-melt pressure-sensitive adhesive which may be included in the elastic lane portion, any appropriate hot-melt pressure-sensitive adhesive may be adopted. The number of kinds of the hot-melt pressure-sensitive adhesives which may be included in the elastic lane portion may be only one, or may be two or more. Examples of such hot-melt pressure-sensitive adhesive include a hot-melt pressure-sensitive adhesive containing a styrene-based elastomer and a hot-melt pressure sensitive adhesive containing an olefin-based polymer. Of those, as the hot-melt pressure-sensitive adhesive which may be included in the elastic lane portion, the hot-melt pressure-sensitive adhesive containing a styrene-based polymer is preferred from the viewpoint of enabling the effects of the present invention to be further exhibited. Examples of such styrene-based polymer include a styrene-based polymer containing SIS, a styrene-based polymer containing SBS, hydrogenated products thereof, and blends thereof.

When the hot-melt pressure-sensitive adhesive which may be included in the elastic lane portion contains a styrene-based polymer, the number of kinds of the styrene-based polymers may be only one, or may be two or more.

When the hot-melt pressure-sensitive adhesive which may be included in the elastic lane portion contains a styrene-based polymer, the content of the styrene-based polymer in the hot-melt pressure-sensitive adhesive which may be included in the elastic lane portion is preferably from 10 wt % to 90 wt %, more preferably from 20 wt % to 80 wt %, still more preferably from 30 wt % to 70 wt %, particularly preferably from 40 wt % to 60 wt % from the viewpoint of enabling the effects of the present invention to be further exhibited.

As the hot-melt pressure-sensitive adhesive which may be included in the rigid lane portion, any appropriate hot-melt pressure-sensitive adhesive may be adopted. The number of kinds of the hot-melt pressure-sensitive adhesives which may be included in the rigid lane portion may be only one, or may be two or more. Examples of such hot-melt pressure-sensitive adhesive include a hot-melt pressure sensitive adhesive containing a styrene-based elastomer and a hot-melt pressure-sensitive adhesive containing an olefin-based polymer. Of those, as the hot-melt pressure-sensitive adhesive which may be included in the rigid lane portion, the hot-melt pressure-sensitive adhesive containing an olefin-based polymer is preferred from the viewpoint of enabling the effects of the present invention to be further exhibited. An example of the hot-melt pressure-sensitive adhesive containing an olefin-based polymer is a hot-melt pressure-sensitive adhesive containing an olefin-based polymer and the same kind of polymer as the elastomer resin forming the elastomer layer. For example, when the elastomer resin forming the elastomer layer is a styrene-based elastomer, as the hot-melt pressure-sensitive adhesive containing an olefin-based polymer, a hot-melt pressure-sensitive adhesive containing an olefin-based polymer and a styrene-based polymer may be adopted. As described above, when the hot-melt pressure-sensitive adhesive containing an olefin-based polymer and the same kind of polymer as the elastomer resin forming the elastomer layer is adopted as the hot-melt pressure-sensitive adhesive containing an olefin-based polymer, the adhesive property between the elastomer layer and the hot-melt pressure-sensitive adhesive can be improved.

When the hot-melt pressure-sensitive adhesive which may be included in the rigid lane portion contains an olefin-based polymer, the number of kinds of the olefin-based polymers may be only one, or may be two or more.

When the hot-melt pressure-sensitive adhesive which may be included in the rigid lane portion contains an olefin-based polymer, the content of the olefin-based polymer in the hot-melt pressure-sensitive adhesive which may be included in the rigid lane portion is preferably from 10 wt % to 90 wt %, more preferably from 20 wt % to 80 wt %, still more preferably from 30 wt % to 70 wt %, particularly preferably from 40 wt % to 60 wt % from the viewpoint of enabling the effects of the present invention to be further exhibited.

Examples of the olefin-based polymer include: a polyolefin resin, such as an olefin-based elastomer, a 1-butene copolymer, amorphous poly-α-olefin, a propylene-based polymer, polyethylene, or an olefin-based thermoplastic elastomer (TPO), and modified products thereof; a copolymer of an α-olefin with a vinyl compound (for example, vinyl acetate or a (meth)acrylic acid ester); polyamide; polyester; polycarbonate; polyurethane; and polyvinyl chloride. Examples of the propylene-based polymer include homopolypropylene, block polypropylene, and random polypropylene. Of those, from the viewpoint of enabling the effects of the present invention to be further exhibited, an olefin-based elastomer, a 1-butene copolymer, or amorphous poly-α-olefin is preferred, a 1-butene copolymer is more preferred, and a propylene/1-butene copolymer described below is still more preferred.

As the olefin-based elastomer, any appropriate olefin-based elastomer may be adopted to the extent that the effects of the present invention are not impaired. Examples of such olefin-based elastomer include an α-olefin-based elastomer, an olefin block copolymer, an olefin random copolymer, an ethylene copolymer, a propylene copolymer, an ethylene olefin block copolymer, a propylene olefin block copolymer, an ethylene olefin random copolymer, a propylene olefin random copolymer, an ethylene propylene random copolymer, an ethylene(1-butene) random copolymer, an ethylene(1-pentene) olefin block copolymer, an ethylene(1-hexene) random copolymer, an ethylene(1-heptene)olefin block copolymer, an ethylene(1-octene)olefin block copolymer, an ethylene(1-nonene)olefin block copolymer, an ethylene(1-decene)olefin block copolymer, a propylene ethylene olefin block copolymer, an ethylene(α-olefin) copolymer, an ethylene(α-olefin) random copolymer, an ethylene(α-olefin) block copolymer, and combinations thereof. Of those, from the viewpoint of enabling the effects of the present invention to be further exhibited, an α-olefin-based elastomer is preferred. The number of kinds of the olefin-based elastomers may be only one, or may be two or more.

A preferred example of the α-olefin-based elastomer is at least one kind selected from an ethylene based elastomer, a propylene-based elastomer, and a 1-butene-based elastomer.

The α-olefin-based elastomer is also available as a commercial product. Examples of such commercial product include some products in the "TAFMER" (trademark) series (such as TAFMER PN-3560) manufactured by Mitsui Chemicals, Inc., some products in the "VISTAMAXX" (trademark) series (such as VISTAMAXX 3000, VISTAMAXX 6202, VISTAMAXX 7010, andVISTAMAXX 7050) manufactured by ExxonMobil Corporation, some products in the "REXtac" (trademark) series (such as REXTAC RT2780 and REXTAC RT2788) manufactured by REXtac, LLC, and products in the TAFTHREN series (such as T3712 and T3522) manufactured by Sumitomo Chemical Co., Ltd.

In addition, as the olefin-based hot-melt pressure-sensitive adhesive, a product with the trade name "AC600" manufactured by Bento Bantçilik may also be used.

As the 1-butene copolymer, any appropriate 1-butene copolymer may be adopted to the extent that the effects of the present invention are not impaired. Examples of such 1-butene copolymer include an ethylene/1-butene copolymer and a propylene/1-butene copolymer. Of those, a propylene/1-butene copolymer is preferred from the viewpoint of enabling the effects of the present invention to be further exhibited. The number of kinds of the 1-butene copolymers may be only one, or may be two or more.

The 1-butene copolymer is also available as a commercial product. Examples of such commercial product include some products in the "Rextac" (trademark) series (such as REXTAC RT2780 and REXTAC RT2788) manufactured by REXtac, LLC.

The hot-melt pressure-sensitive adhesive may contain any appropriate other component to the extent that the effects of the present invention are not impaired. Examples of such other component include liquid paraffin, a tackifier, an antioxidant, a UV absorber, a light stabilizer, and a fluorescence agent. The number of kinds of such other components may be only one, or may be two or more.

The tackifier is effective for improving a pressure-sensitive adhesive strength. When the hot-melt pressure-sensitive adhesive contains the tackifier, the content of the tackifier in the hot-melt pressure-sensitive adhesive is preferably from 10 wt % to 90 wt %, more preferably from 20 wt % to 80 wt %, still more preferably from 30 wt % to 70 wt %, particularly preferably from 40 wt % to 60 wt % from the viewpoint of enabling the effects of the present invention to be further exhibited.

Examples of the tackifier include a hydrocarbon-based tackifier, a terpene-based tackifier, a rosin-based tackifier, a phenol-based tackifier, an epoxy-based tackifier, a polyamide-based tackifier, an elastomer-based tackifier, and a ketone-based tackifier. The number of kinds of the tackifiers may be only one, or may be two or more.

Examples of the hydrocarbon-based tackifier include an aliphatic hydrocarbon resin, an aromatic hydrocarbon resin (such as a xylene resin), an aliphatic cyclic hydrocarbon resin, an aliphatic aromatic petroleum resin (such as a styrene-olefin copolymer), an aliphatic alicyclic petroleum resin, a hydrogenated hydrocarbon resin, a coumarone-based resin, and a coumarone-indene-based resin.

Examples of the terpene-based tackifier include: a terpene based resin, such as an α-pinene polymer or a β-pinene polymer; and a modified terpene-based resin which is obtained through modification of a terpene-based resin (for example, through phenol modification, aromatic modification, or hydrogenation modification) (such as a terpene-phenol-based resin, a styrene-modified terpene-based resin, or a hydrogenated terpene-based resin).

Examples of the rosin-based tackifier include: an unmodified rosin (raw rosin), such as gum rosin or wood rosin; a modified rosin which is obtained by modifying an unmodified rosin by hydrogenation, disproportionation, polymerization, or the like (such as a hydrogenated rosin, a disproportionated rosin, a polymerized rosin, or other chemically modified rosins); and other rosin derivatives.

An example of the phenol-based tackifier is a resol-type or novolac-type alkylphenol.

The tackifier may be a product commercially available as a blend with an olefin resin or a thermoplastic elastomer.

<<Production of Stretchable Laminate of the Present Invention>>

In production of the stretchable laminate of the present invention, the elastomer layer and the non-woven fabric layer are directly laminated with each other (for example, FIG. 1), and hence the elastomer layer and the non-woven fabric layer need to be bonded onto each other. Examples of such bonding method include: (1) a method involving laminating an elastomer layer formed by extrusion molding from a T-die of an extruder and a non-woven fabric layer separately fed from a rolled body; (2) a method involving laminating an elastomer layer and a non-woven fabric layer by co-extrusion; (3) a method involving bonding an elastomer layer and a non-woven fabric layer, which are prepared separately, with an adhesive; (4) a method involving forming a non-woven fabric layer on an elastomer layer, which has been formed by any appropriate method, by a melt-blown method or the like; and (5) thermally laminating or ultrasonically welding an elastomer layer and a non-woven fabric layer.

In production of the stretchable laminate of the present invention, the hot-melt pressure-sensitive adhesive is preferably used for bonding the elastomer layer and the non-woven fabric layer onto each other. For example, in the case of applying the method (1) described above, the non-woven fabric layer separately fed from a rolled body may be coated with the hot-melt pressure-sensitive adhesive before being laminated with the elastomer layer. In this case, the non-woven fabric layer may be preferably coated with the hot-melt pressure-sensitive adhesive which may be included in the elastic lane portion and the hot-melt pressure-sensitive adhesive which may be included in the rigid lane portion as in a hot-melt pressure-sensitive adhesive containing a styrene-based elastomer (such as an SIS-based hot-melt pressure-sensitive adhesive) and a hot-melt pressure-sensitive adhesive containing an olefin-based polymer (such as an olefin-based hot-melt pressure-sensitive adhesive), respectively.

The stretchable laminate of the present invention can be subjected to treatments referred to as pre-extension treatment and activation treatment after laminating the elastomer layer and the non-woven fabric layer. Specifically, extension treatment is performed in a width direction of the stretchable laminate or treatment in which a fiber structure of a part of the region of the non-woven fabric layer is mechanically broken can be performed. When such treatments are performed, the stretchable laminate can be elongated by a smaller force.

<<Application of Stretchable Laminate of the Present Invention>>

The stretchable laminate of the present invention can be used in any appropriate article in which the effects of the present invention can be effectively utilized. That is, the article of the present invention includes the stretchable laminate of the present invention. A typical example of such article is a sanitary article. Examples of such sanitary article include a diaper (particularly an ear portion of a disposal diaper), a supporter, and a mask.

EXAMPLES

The present invention is hereinafter specifically described by way of Examples. However, the present invention is by no means limited by these Examples. In Examples and the like, test and evaluation methods are as described below. In addition, "part(s)" means "part (s) by weight" and "%" means "wt o" unless otherwise stated.

<Evaluation of End Portion Strength (Strength Required for Obtaining a 5% Deformation Amount of Rigid Lane Portion)>

A stretchable laminate including a rigid lane having a width of 50 mm before slitting was cut into a size of 20 mm in width and 10 cm in length so that a vertical direction (cross-machine direction (CD)) with respect to a film flow direction (machine direction (MD)) formed a long side. One side of the resultant stretchable laminate was chucked at 5 mm from an end portion thereof so that the end portion was located between chucks. The other side was set on a tension testing machine (manufactured by Shimadzu Corporation: AG-20kNG) so as to have a distance between chucks of 33 mm, and thus an extension test was performed at a tension speed of 500 mm/min. The tensile strength at a time of an extension of 5% between the chucks was defined as end portion strength. Measurement was performed at N=5, and an average value was defined as end portion strength.

<Test of Holding Ability>

Figure 3:
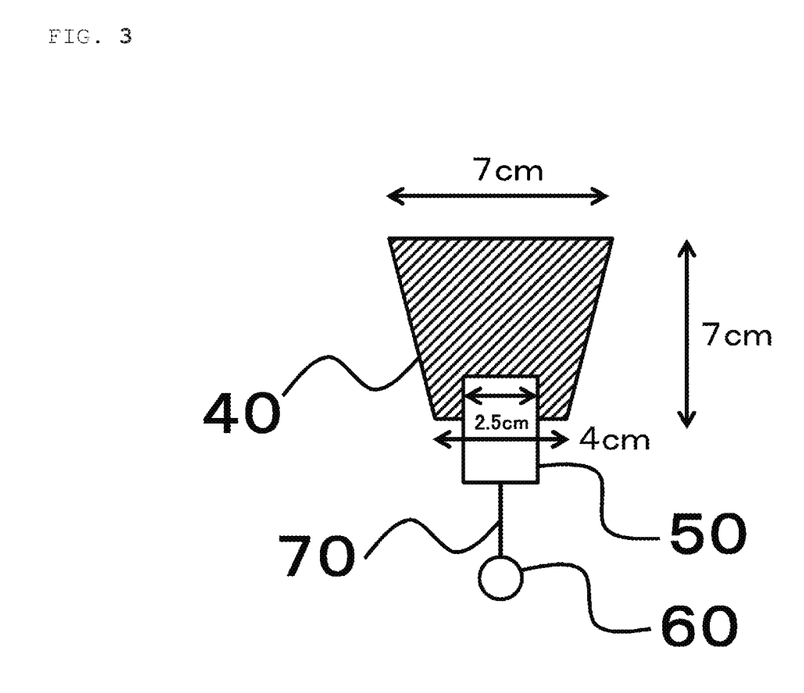
FIG. 3 is a schematic view for illustrating a holding ability test.

As illustrated in FIG. 3, a stretchable laminate to be measured was cut out into a trapezoidal shape (40) having an upper base of 7 cm, a lower base of 4 cm, and a height of 7 cm, and a side tape (manufactured by Nitto Bento Bantçi- lik, trade name: SB50WN1-06) (50) cut out into a size of 2.5 cm in length was bonded onto a lower base side by 20 times of lamination at a speed of 300 mm/min through use of a 20 kg roller so that an area of 2.5 cm×2.8 cm was bonded as illustrated in FIG. 3 to provide a sample for evaluation. Five samples for evaluation were produced. A load (60) of 1 kg was suspended on each side tape of the resultant five samples for evaluation through use of a stainless-steel bar (70) under an environment of 40° C., and the holding property of the bonded portion was evaluated.

○: Under a state of a load of 1 kg at 40° C., the bonded portion was held for 30 minutes or more in all the samples.

×: Under a state of a load of 1 kg at 40° C., the side tape fell within less than 30 minutes due to peeling of the bonded portion in at least one sample.

<Test of Feeling of Touch>

The stretchable laminate was mounted to a diaper (trapezoidal shape having a diaper body-side adhesion width of 7 cm and a side tape-side width of 4 cm), and the feeling of touch of a portion at a corner of the stretchable laminate adjacent to the side tape was evaluated.

○: No pain was felt.

×: Pain was felt.

<Molding Method>

In Examples and Comparative Example 1, an elastomer layer (hereinafter sometimes referred to as elastic film) was formed by extrusion molding by extruding three layers in two types (A layer/B layer/A layer) through the use of a T-die molding machine. The extrusion temperatures were set under the following conditions.

A layer: 200° C.
B layer: 200° C.
Die temperature: 200° C.

Non-woven fabric was bonded onto both surfaces of the elastic film extruded from the T-die through use of a roll to provide a stretchable laminate. In this case, a hot-melt pressure-sensitive adhesive was applied onto a bonded side of the non-woven fabric so as to alternately have a portion (A) in which the hot-melt pressure-sensitive adhesive had been applied onto the whole surface with a width of 50 mm and a portion (B) in which the hot-melt pressure-sensitive adhesive was applied in a striped manner (pressure-sensitive adhesive width: 1 mm, interval: 1 mm) with a width of 31 mm.

Example 1

A formulation of 97 wt % of an SIS-based resin (manufactured by Zeon Corporation, trade name: Quintac 3390, styrene content=48%, MFR=15.0 g/10 min) and 3 wt % of a white pigment (titanium oxide, manufactured by Dupont, trade name: Ti-Pure R103) was loaded into A layer and B layer in an extrusion machine to extrude an elastic film having the construction of A layer/B layer/A layer=7 μm/31 μm/7 μm in total of 45 μm. Next, an SIS-based hot-melt pressure-sensitive adhesive (manufactured by Bento Bantçilik, trade name: AC280) was applied onto an elastic lane in a striped manner (pressure-sensitive adhesive layer width: 1 mm, interval: 1 mm) at 12 g/m². Meanwhile, an olefin-based hot-melt pressure-sensitive adhesive (manufactured by Bento Bantçilik, trade name: AC600) was applied onto a rigid lane with a width of 50 mm at 10 g/m². Both surfaces of the elastic film were bonded onto a non-woven fabric (PP spunlace type, basis weight: 30 g/m²). Further, a portion (A) in which the hot-melt pressure-sensitive adhesive had been applied onto the whole surface (10 g/m²) with a width of 50 mm was cut at the middle, and both end portions were slit by 10 mm. Thus, a stretchable laminate having two portions (A1) and (A2), in which the hot-melt pressure-sensitive adhesive had been applied onto the whole surface (10 g/m²) with a width of 15 mm from both ends, and a portion (B), in which the hot-melt pressure-sensitive adhesive had been applied (12 g/m²) between the (A1) and the (A2) with a width of 31 mm in a striped manner (pressure-sensitive adhesive width: 1 mm, interval: 1 mm), on both surfaces of the elastic film was obtained.

The results are shown in Table 1.

Example 2

A formulation of 97 wt % of an SIS-based resin (manufactured by Zeon Corporation, trade name: Quintac 3390, styrene content=48%, MFR=15.0 g/10 min) and 3 wt % of a white pigment (titanium oxide, manufactured by Dupont, trade name: Ti-Pure R103) was loaded into A layer and B layer in an extrusion machine to extrude an elastic film having the construction of A layer/B layer/A layer=9 μm/37 μm/9 μm in total of 55 μm. Next, an SIS-based hot-melt pressure-sensitive adhesive (manufactured by Bento Bantçilik, trade name: AC280) was applied onto an elastic lane in a striped manner (pressure-sensitive adhesive layer width: 1 mm, interval: 1 mm) at 12 g/m². Meanwhile, an olefin-based hot-melt pressure-sensitive adhesive (manufactured by Bento Bantçilik, trade name: AC600) was applied onto a rigid lane with a width of 50 mm at 12 g/m². Both surfaces of the elastic film were bonded onto a non-woven fabric (PP spunlace type, basis weight: 30 g/m²). Further, a portion (A) in which the hot-melt pressure-sensitive adhesive had been applied onto the whole surface (12 g/m²) with a width of 50 mm was cut at the middle, and both end portions were slit by 10 mm. Thus, a stretchable laminate having two portions (A1) and (A2), in which the hot-melt pressure-sensitive adhesive had been applied onto the whole surface (12 g/m²) with a width of 15 mm from both ends, and a portion (B), in which the hot-melt pressure-sensitive adhesive had been applied (12 g/m²) between the (A1) and the (A2) with a width of 31 mm in a striped manner (pressure-sensitive adhesive width: 1 mm, interval: 1 mm), on both surfaces of the elastic film was obtained.

The results are shown in Table 1.

Example 3

A formulation of 97 wt % of an SIS-based resin (manufactured by Zeon Corporation, trade name: Quintac 3390, styrene content=48%, MFR=15.0 g/10 min) and 3 wt % of a white pigment (titanium oxide, manufactured by Dupont, trade name: Ti-Pure R103) was loaded into A layer and B layer in an extrusion machine to extrude an elastic film having the construction of A layer/B layer/A layer=9 μm/37 μm/9 μm in total of 55 μm. Next, an SIS-based hot-melt pressure-sensitive adhesive (manufactured by Bento Bantçilik, trade name: AC280) was applied onto an elastic lane in a striped manner (pressure-sensitive adhesive layer width: 1 mm, interval: 1 mm) at 12 g/m². Meanwhile, an olefin-based hot-melt pressure-sensitive adhesive (manufactured by Bento Bantçilik, trade name: AC600) was applied onto a rigid lane with a width of 50 mm at 15 g/m². Both surfaces of the elastic film were bonded onto a non-woven fabric (PP spunlace type, basis weight: 30 g/m²). Further, a portion (A) in which the hot-melt pressure-sensitive adhesive had been applied onto the whole surface (15 g/m²) with a width of 50 mm was cut at the middle, and both end portions were slit by 10 mm. Thus, a stretchable laminate having two portions (A1) and (A2), in which the hot-melt pressure-sensitive adhesive had been applied onto the whole surface (15 g/m$^2$) with a width of 15 mm from both ends, and a portion (B), in which the hot-melt pressure-sensitive adhesive had been applied (12 g/m$^2$) between the (A1) and the (A2) with a width of 31 mm in a striped manner (pressure-sensitive adhesive width: 1 mm, interval: 1 mm), on both surfaces of the elastic film was obtained.

The results are shown in Table 1.

Example 4

A formulation of 97 wt % of an SIS-based resin (manufactured by Zeon Corporation, trade name: Quintac 3390, styrene content=48%, MFR=15.0 g/10 min) and 3 wt % of a white pigment (titanium oxide, manufactured by Dupont, trade name: Ti-Pure R103) was loaded into A layer and B layer in an extrusion machine to extrude an elastic film having the construction of A layer/B layer/A layer=7 µm/31 µm/7 µm in total of 45 µm. Next, an SIS-based hot-melt pressure-sensitive adhesive (manufactured by Bento Bantçilik, trade name: AC280) was applied onto an elastic lane in a striped manner (pressure-sensitive adhesive layer width: 1 mm, interval: 1 mm) at 12 g/m$^2$.

Next, 100 parts by weight of a propylene/1-butene copolymer (manufactured by REXtac, LLC, trade name: REXTAC RT2788), 200 parts by weight of a styrene-based polymer (manufactured by Kraton Performance Polymers, Inc., trade name: KRATON D1163), 600 parts by weight of a tackifier (manufactured by Kolon Chem. Co., Ltd., trade name: SUKOREZ SU-100S), 90 parts by weight of liquid paraffin (manufactured by Petro yag, trade name: White Oil Pharma Oyster 259), and 10 parts by weight of an antioxidant (manufactured by BASF Japan Co., Ltd., trade name: Irganox 1010) were blended to provide a hot-melt pressure-sensitive adhesive (X).

The hot-melt pressure-sensitive adhesive (X) was applied onto a rigid lane with a width of 50 mm at 16 g/m$^2$, and both surfaces of the elastic film were bonded onto a non-woven fabric (PP spunlace type, basis weight: 30 g/m$^2$). Further, a portion (A) in which the hot-melt pressure-sensitive adhesive had been applied onto the whole surface (16 g/m$^2$) with a width of 50 mm was cut at the middle, and both end portions were slit by 10 mm. Thus, a stretchable laminate having two portions (A1) and (A2), in which the hot-melt pressure-sensitive adhesive had been applied onto the whole surface (16 g/m$^2$) with a width of 15 mm from both ends, and a portion (B), in which the hot-melt pressure-sensitive adhesive had been applied (12 g/m$^2$) between the (A1) and the (A2) with a width of 31 mm in a striped manner (pressure-sensitive adhesive width: 1 mm, interval: 1 mm), on both surfaces of the elastic film was obtained.

The results are shown in Table 1.

Example 5

A formulation of 97 wt % of an SIS-based resin (manufactured by Zeon Corporation, trade name: Quintac 3390, styrene content=48%, MFR=15.0 g/10 min) and 3 wt % of a white pigment (titanium oxide, manufactured by Dupont, trade name: Ti-Pure R103) was loaded into A layer and B layer in an extrusion machine to extrude an elastic film having the construction of A layer/B layer/A layer=9 µm/37 µm/9 µm in total of 55 µm. Next, an SIS-based hot-melt pressure-sensitive adhesive (manufactured by Bento Bantçilik, trade name: AC280) was applied onto an elastic lane in a striped manner (pressure-sensitive adhesive layer width: 1 mm, interval: 1 mm) at 12 g/m$^2$.

Next, 100 parts by weight of a propylene/1-butene copolymer (manufactured by REXtac, LLC, trade name: REXTAC RT2788), 200 parts by weight of a styrene-based polymer (manufactured by Kraton Performance Polymers, Inc., trade name: KRATON D1163), 600 parts by weight of a tackifier (manufactured by Kolon Chem. Co., Ltd., trade name: SUKOREZ SU-100S), 90 parts by weight of liquid paraffin (manufactured by Petro yag, trade name: White Oil Pharma Oyster 259), and 10 parts by weight of an antioxidant (manufactured by BASF Japan Co., Ltd., trade name: Irganox 1010) were blended to provide a hot-melt pressure-sensitive adhesive (X).

The hot-melt pressure-sensitive adhesive (X) was applied onto a rigid lane with a width of 50 mm at 17 g/m$^2$, and both surfaces of the elastic film were bonded onto a non-woven fabric (PP spunlace type, basis weight: 30 g/m$^2$). Further, a portion (A) in which the hot-melt pressure-sensitive adhesive had been applied onto the whole surface (17 g/m$^2$) with a width of 50 mm was cut at the middle, and both end portions were slit by 10 mm. Thus, a stretchable laminate having two portions (A1) and (A2), in which the hot-melt pressure-sensitive adhesive had been applied onto the whole surface (17 g/m$^2$) with a width of 15 mm from both ends, and a portion (B), in which the hot-melt pressure-sensitive adhesive had been applied (12 g/m$^2$) between the (A1) and the (A2) with a width of 31 mm in a striped manner (pressure-sensitive adhesive width: 1 mm, interval: 1 mm), on both surfaces of the elastic film was obtained.

The results are shown in Table 1.

Example 6

A formulation of 97 wt % of an SIS-based resin (manufactured by Zeon Corporation, trade name: Quintac 3390, styrene content=48%, MFR=15.0 g/10 min) and 3 wt % of a white pigment (titanium oxide, manufactured by Dupont, trade name: Ti-Pure R103) was loaded into A layer and B layer in an extrusion machine to extrude an elastic film having the construction of A layer/B layer/A layer=9 µm/37 µm/9 µm in total of 55 µm. Next, an SIS-based hot-melt pressure-sensitive adhesive (manufactured by Bento Bantçilik, trade name: AC280) was applied onto an elastic lane in a striped manner (pressure-sensitive adhesive layer width: 1 mm, interval: 1 mm) at 12 g/m$^2$.

Next, 100 parts by weight of a propylene/1-butene copolymer (manufactured by REXtac, LLC, trade name: REXTAC RT2788), 200 parts by weight of a styrene-based polymer (manufactured by Kraton Performance Polymers, Inc., trade name: KRATON D1163), 600 parts by weight of a tackifier (manufactured by Kolon Chem. Co., Ltd., trade name: SUKOREZ SU-100S), 90 parts by weight of liquid paraffin (manufactured by Petro yag, trade name: White Oil Pharma Oyster 259), and 10 parts by weight of an antioxidant (manufactured by BASF Japan Co., Ltd., trade name: Irganox 1010) were blended to provide a hot-melt pressure-sensitive adhesive (X).

The hot-melt pressure-sensitive adhesive (X) was applied onto a rigid lane with a width of 50 mm at 25 g/m$^2$, and both surfaces of the elastic film were bonded onto a non-woven fabric (PP spunlace type, basis weight: 30 g/m$^2$). Further, a portion (A) in which the hot-melt pressure-sensitive adhesive had been applied onto the whole surface (25 g/m$^2$) with a width of 50 mm was cut at the middle, and both end portions were slit by 10 mm. Thus, a stretchable laminate having two portions (A1) and (A2), in which the hot-melt pressure-sensitive adhesive had been applied onto the whole surface (25 g/m²) with a width of 15 mm from both ends, and a portion (B), in which the hot-melt pressure-sensitive adhesive had been applied (12 g/m²) between the (A1) and the (A2) with a width of 31 mm in a striped manner (pressure-sensitive adhesive width: 1 mm, interval: 1 mm), on both surfaces of the elastic film was obtained.

The results are shown in Table 1.

Example 7

A formulation of 97 wt % of an SIS-based resin (manufactured by Zeon Corporation, trade name: Quintac 3390, styrene content=48%, MFR=15.0 g/10 min) and 3 wt % of a white pigment (titanium oxide, manufactured by Dupont, trade name: Ti-Pure R103) was loaded into A layer and B layer in an extrusion machine to extrude an elastic film having the construction of A layer/B layer/A layer=7 μm/31 μm/7 μm in total of 45 μm. Next, an SIS-based hot-melt pressure-sensitive adhesive (manufactured by Bento Bantçilik, trade name: AC280) was applied onto an elastic lane in a striped manner (pressure-sensitive adhesive layer width: 1 mm, interval: 1 mm) at 12 g/m².

Next, 100 parts by weight of a propylene/1-butene copolymer (manufactured by REXtac, LLC, trade name: REXTAC RT2788), 200 parts by weight of a styrene-based polymer (manufactured by Kraton Performance Polymers, Inc., trade name: KRATON D1163), 600 parts by weight of a tackifier (manufactured by Kolon Chem. Co., Ltd., trade name: SUKOREZ SU-100S), 90 parts by weight of liquid paraffin (manufactured by Petro yag, trade name: White Oil Pharma Oyster 259), and 10 parts by weight of an antioxidant (manufactured by BASF Japan Co., Ltd., trade name: Irganox 1010) were blended to provide a hot-melt pressure-sensitive adhesive (X).

The hot-melt pressure-sensitive adhesive (X) was applied onto a rigid lane with a width of 50 mm at 8 g/m², and both surfaces of the elastic film were bonded onto a non-woven fabric (PP carded type, basis weight: 24 g/m²). Further, a portion (A) in which the hot-melt pressure-sensitive adhesive had been applied onto the whole surface (8 g/m²) with a width of 50 mm was cut at the middle, and both end portions were slit by 10 mm. Thus, a stretchable laminate having two portions (A1) and (A2), in which the hot-melt pressure-sensitive adhesive had been applied onto the whole surface (8 g/m²) with a width of 15 mm from both ends, and a portion (B), in which the hot-melt pressure-sensitive adhesive had been applied (12 g/m²) between the (A1) and the (A2) with a width of 31 mm in a striped manner (pressure-sensitive adhesive width: 1 mm, interval: 1 mm), on both surfaces of the elastic film was obtained.

The results are shown in Table 1.

Example 8

A formulation of 97 wt % of an SIS-based resin (manufactured by Zeon Corporation, trade name: Quintac 3390, styrene content=48%, MFR=15.0 g/10 min) and 3 wt % of a white pigment (titanium oxide, manufactured by Dupont, trade name: Ti-Pure R103) was loaded into A layer and B layer in an extrusion machine to extrude an elastic film having the construction of A layer/B layer/A layer=7 μm/31 μm/7 μm in total of 45 μm. Next, an SIS-based hot-melt pressure-sensitive adhesive (manufactured by Bento Bantçilik, trade name: AC280) was applied onto an elastic lane in a striped manner (pressure-sensitive adhesive layer width: 1 mm, interval: 1 mm) at 12 g/m².

Next, 100 parts by weight of a propylene/1-butene copolymer (manufactured by REXtac, LLC, trade name: REXTAC RT2788), 200 parts by weight of a styrene-based polymer (manufactured by Kraton Performance Polymers, Inc., trade name: KRATON D1163), 600 parts by weight of a tackifier (manufactured by Kolon Chem. Co., Ltd., trade name: SUKOREZ SU-100S), 90 parts by weight of liquid paraffin (manufactured by Petro yag, trade name: White Oil Pharma Oyster 259), and 10 parts by weight of an antioxidant (manufactured by BASF Japan Co., Ltd., trade name: Irganox 1010) were blended to provide a hot-melt pressure-sensitive adhesive (X).

The hot-melt pressure-sensitive adhesive (X) was applied onto a rigid lane with a width of 50 mm at 16 g/m², and both surfaces of the elastic film were bonded onto a non-woven fabric (PP carded type, basis weight: 24 g/m²). Further, a portion (A) in which the hot-melt pressure-sensitive adhesive had been applied onto the whole surface (16 g/m²) with a width of 50 mm was cut at the middle, and both end portions were slit by 10 mm. Thus, a stretchable laminate having two portions (A1) and (A2), in which the hot-melt pressure-sensitive adhesive had been applied onto the whole surface (16 g/m²) with a width of 15 mm from both ends, and a portion (B), in which the hot-melt pressure-sensitive adhesive had been applied (12 g/m²) between the (A1) and the (A2) with a width of 31 mm in a striped manner (pressure-sensitive adhesive width: 1 mm, interval: 1 mm), on both surfaces of the elastic film was obtained.

The results are shown in Table 1.

Comparative Example 1

A formulation of 97 wt % of an SIS-based resin (manufactured by Zeon Corporation, trade name: Quintac 3390, styrene content=48%, MFR=15.0 g/10 min) and 3 wt % of a white pigment (titanium oxide, manufactured by Dupont, trade name: Ti-Pure R103) was loaded into A layer and B layer in an extrusion machine to extrude an elastic film having the construction of A layer/B layer/A layer=9 μm/37 μm/9 μm in total of 55 μm. Next, an SIS-based hot-melt pressure-sensitive adhesive (manufactured by Bento Bantçilik, trade name: AC280) was applied onto an elastic lane in a striped manner (pressure-sensitive adhesive layer width: 1 mm, interval: 1 mm) at 12 g/m². Meanwhile, an SIS-based hot-melt pressure-sensitive adhesive (manufactured by Bento Bantçilik, trade name: AC280) was applied onto a rigid lane with a width of 50 mm at 12 g/m². Both surfaces of the elastic film were bonded onto a non-woven fabric (PP spunlace type, basis weight: 30 g/m²). Further, a portion (A) in which the hot-melt pressure-sensitive adhesive had been applied onto the whole surface (12 g/m²) with a width of 50 mm was cut at the middle, and both end portions were slit by 10 mm. Thus, a stretchable laminate having two portions (A1) and (A2), in which the hot-melt pressure-sensitive adhesive had been applied onto the whole surface (12 g/m²) with a width of 15 mm from both ends, and a portion (B), in which the hot-melt pressure-sensitive adhesive had been applied (12 g/m²) between the (A1) and the (A2) with a width of 31 mm in a striped manner (pressure-sensitive adhesive width: 1 mm, interval: 1 mm), on both surfaces of the elastic film was obtained.

The results are shown in Table 1.

Comparative Example 2

A PET-based film (manufactured by Teijin DuPont Films Japan Limited, G2, thickness: 50 μm) was used for an elastomer layer. Next, an SIS-based hot-melt pressure-sensitive adhesive (manufactured by Bento Bantçilik, trade name: AC280) was applied onto an elastic lane in a striped manner (pressure-sensitive adhesive layer width: 1 mm, interval: 1 mm) at 12 g/m². Meanwhile, an olefin-based hot-melt pressure-sensitive adhesive (manufactured by Bento Bantçilik, trade name: AC600) was applied onto a rigid lane with a width of 50 mm at 15 g/m². Both surfaces of the elastic film were bonded onto a non-woven fabric (PP spunlace type, basis weight: 30 g/m²). Further, a portion (A) in which the hot-melt pressure-sensitive adhesive had been applied onto the whole surface (15 g/m²) with a width of 50 mm was cut at the middle, and both end portions were slit by 10 mm. Thus, a stretchable laminate having two portions (A1) and (A2), in which the hot-melt pressure-sensitive adhesive had been applied onto the whole surface (15 g/m²) with a width of 15 mm from both ends, and a portion (B), in which the hot-melt pressure-sensitive adhesive had been applied (12 g/m²) between the (A1) and the (A2) with a width of 31 mm in a striped manner (pressure-sensitive adhesive width: 1 mm, interval: 1 mm), on both surfaces of the elastic film was obtained.

The results are shown in Table 1.

21a non-woven fabric layer
21b non-woven fabric layer
22a non-woven fabric layer
22b non-woven fabric layer
30 hot-melt pressure-sensitive adhesive
31a hot-melt pressure-sensitive adhesive
31b hot-melt pressure-sensitive adhesive
32a hot-melt pressure-sensitive adhesive
32b hot-melt pressure-sensitive adhesive
40 stretchable laminate cut out into trapezoidal shape
50 side tape
60 load
70 stainless-steel bar

The invention claimed is:

1. A stretchable laminate, comprising:
an elastomer layer;
a non-woven fabric layer arranged on at least one side of the elastomer layer, and
the stretchable laminate including an elastic lane portion and a rigid lane portion,
the rigid lane portion requiring a strength of from 1 N/20 mm to 7 N/20 mm for obtaining a 5% deformation amount,

TABLE 1

|  | Example 1 | Example 2 | Example 3 | Example 4 | Example 5 | Example 6 | Example 7 | Example 8 | Comparative Example 1 | Comparative Example 2 |
|---|---|---|---|---|---|---|---|---|---|---|
| Elastomer layer | Styrene-based 45 μm | Styrene-based 55 μm | Styrene-based 55 μm | Styrene-based 45 μm | Styrene-based 55 μm | Styrene-based 55 μm | Styrene-based 45 μm | Styrene-based 45 μm | Styrene-based 55 μm | PET-based 50 μm |
| Hot-melt pressure-sensitive adhesive on elastic lane | Styrene-based | Styrene-based | Styrene-based | Styrene-based | Styrene-based | Styrene-based | Styrene-based | Styrene-based | Styrene-based | Styrene-based |
| Hot-melt pressure-sensitive adhesive on rigid lane | Olefin-based | Olefin-based | Olefin-based | Olefin-based + styrene-based | Olefin-based + styrene-based | Olefin-based + styrene-based | Olefin-based + styrene-based | Olefin-based + styrene-based | Styrene-based | Olefin-based |
| Non-woven fabric layer | Spunlace 30 g/m² | Spunlace 30 g/m² | Spunlace 30 g/m² | Spunlace 30 g/m² | Spunlace 30 g/m² | Spunlace 30 g/m² | Carded 24 g/m² | Carded 24 g/m² | Spunlace 30 g/m² | Spunlace 30 g/m² |
| End portion strength (N/20 mm) | 1.5 | 2.2 | 2.5 | 1.2 | 2.3 | 3.3 | 2.0 | 3.7 | 0.6 | 10 |
| Holding ability | ○ | ○ | ○ | ○ | ○ | ○ | ○ | ○ | X | ○ |
| Feeling of touch | ○ | ○ | ○ | ○ | ○ | ○ | ○ | ○ | ○ | X |

INDUSTRIAL APPLICABILITY

The stretchable laminate of the present invention may be used in any appropriate article in which the effects of the present invention can be effectively utilized. That is, the article of the present invention includes the stretchable laminate of the present invention. A typical example of such article is a sanitary article. Examples of such sanitary article include a diaper (particularly, an ear portion of a disposal diaper), a supporter, and a mask.

REFERENCE SIGNS LIST 100 stretchable laminate
110 elastic lane portion
120 rigid lane portion
10 elastomer layer
20 non-woven fabric layer wherein the rigid lane portion includes a first portion of the elastomer layer, a first portion of the non-woven fabric layer, and a first hot-melt pressure-sensitive adhesive between the first portion of the elastomer layer and the first portion of the non-woven fabric, and
the elastic lane portion includes a second portion of the elastomer layer, a second portion of the non-woven fabric layer, and a second hot-melt pressure-sensitive adhesive between the second portion of the elastomer layer and the second portion of the non-woven fabric layer,
and
wherein the second hot-melt pressure-sensitive adhesive consists of a styrene-based elastomer and the first hot-melt pressure-sensitive adhesive consists of an olefin-based polymer and a styrene-based polymer.

2. The stretchable laminate according to claim 1, wherein the rigid lane portion requires a strength of from 1 N/20 mm to 4 N/20 mm for obtaining a 5% deformation amount.

3. The stretchable laminate according to claim 1, wherein the rigid lane portion comprises an end portion of the stretchable laminate.

4. The stretchable laminate according to claim 3, wherein the rigid lane portion has a length from the end portion of the stretchable laminate of from 5 mm to 30 mm.

5. The stretchable laminate according to claim 1, wherein the olefin-based polymer comprises a propylene/1-butene copolymer.

6. The stretchable laminate according to claim 1, wherein the first hot-melt pressure-sensitive adhesive in the rigid lane portion contains the olefin-based polymer and the same kind of polymer as an elastomer resin forming the elastomer layer.

7. The stretchable laminate according to claim 6, wherein the polymer of the same kind as the elastomer resin forming the elastomer layer comprises a styrene-based polymer.

8. The stretchable laminate according to claim 1, wherein the styrene-based polymer contains SIS.

9. The stretchable laminate according to claim 1, wherein the second hot-melt pressure-sensitive adhesive in the elastic lane portion has a stripe shape.

10. The stretchable laminate according to claim 1, wherein the elastomer layer contains a styrene-based elastomer.

11. The stretchable laminate according to claim 10, wherein the styrene-based elastomer comprises an SIS-based elastomer.

12. The stretchable laminate according to claim 11, wherein a content of styrene is from 3 wt % to 60 wt % in the SIS-based elastomer.

13. The stretchable laminate according to claim 12, wherein a content of styrene is from 10 wt % to 50 wt % in the SIS-based elastomer.

14. The stretchable laminate according to claim 11, wherein the SIS-based elastomer has a MFR of from 5.0 g/10 min to 25.0 g/10 min.

15. The stretchable laminate according to claim 14, wherein the SIS-based elastomer has a MFR of from 8.0 g/10 min to 18.0 g/10 min.

16. The stretchable laminate according to claim 1, wherein the non-woven fabric layer comprises a spunlace non-woven fabric.

17. An article, comprising the stretchable laminate of claim 1.

18. The stretchable laminate according to claim 1, wherein a content of the styrene-based polymer is 10-90 wt % and a content of the olefin-based polymer is from 10-90 wt %.

19. The stretchable laminate according to claim 1, wherein the elastomer layer contains a styrene-based elastomer.

\* \* \* \* \*